(12) United States Patent
Haley

(10) Patent No.: US 9,227,992 B2
(45) Date of Patent: Jan. 5, 2016

(54) METHOD OF PREPARING DEOXYRIBOFURANOSE COMPOUNDS

(71) Applicant: Anadys Pharmaceuticals, Inc., South San Francisco, CA (US)

(72) Inventor: Gregory J. Haley, San Diego, CA (US)

(73) Assignee: ANADYS PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 14/448,033

(22) Filed: Jul. 31, 2014

(65) Prior Publication Data

US 2014/0350231 A1 Nov. 27, 2014

Related U.S. Application Data

(62) Division of application No. 13/129,730, filed as application No. PCT/US2009/064605 on Nov. 16, 2009, now Pat. No. 8,829,168.

(60) Provisional application No. 61/115,134, filed on Nov. 17, 2008.

(51) Int. Cl.
*C07H 9/04* (2006.01)
*C07D 307/20* (2006.01)

(52) U.S. Cl.
CPC ............... *C07H 9/04* (2013.01); *C07D 307/20* (2013.01)

(58) Field of Classification Search
CPC ............................... C07H 9/04; C07D 307/20
USPC ......................................................... 536/18.1
See application file for complete search history.

(56) References Cited

U.S. PATENT DOCUMENTS

| | | | | |
|---|---|---|---|---|
| 5,880,294 | A * | 3/1999 | Nomura et al. ............... | 549/435 |
| 7,309,717 | B2 | 12/2007 | Park et al. | |
| 2004/0097742 | A1 | 5/2004 | Newsome et al. | |
| 2004/0175808 | A1 | 9/2004 | Savary et al. | |
| 2005/0080252 | A1 | 4/2005 | Briggs et al. | |
| 2005/0090660 | A1* | 4/2005 | Watanabe et al. ............ | 536/27.1 |
| 2007/0225246 | A1 | 9/2007 | Denu et al. | |

FOREIGN PATENT DOCUMENTS

| | | | | |
|---|---|---|---|---|
| CN | 1878783 | A | | 12/2006 |
| CN | 1919858 | A | | 2/2007 |
| CN | 101172989 | A | | 5/2008 |
| JP | 2007137843 | | * | 6/2007 ............. C07H 15/18 |
| WO | 2009/116067 | A2 | | 9/2009 |

OTHER PUBLICATIONS

Yadav et al, Synlett 2000, 9, 1275-76.*
Chevallier et al, Beilstein Journal of Organic Chemistry, 2006, 2(14), 1-6.*
Greene et al, Protective Groups in Organic Synthesis, 2nd Ed., 1991, pp. 87-90.*
International Search Report, International Application No. PCT/US09/64605, mailed Jan. 22, 2010.
Zhu et al., "Preparation of Monoacetylated Diols via Cyclic Ketene Acetals," Journal of Organic Chemistry, 1995, vol. 60, pp. 5279-5731.
Supplementary European Search Report, European Application No. EP09826915.2, mailed Jun. 5, 2012.
Watanabe et al., "Nucleosides. 116. 1-(Beta-D-Xylofuranosyl)-5-fluorocytosines with a Leaving Group on the 3' Position. Potential Double-Barreled Masked Precursors of Anticancer Nucleosides," Journal of Medicinal Chemistry, American Chemical Society, 1980, vol. 23, No. 10, pp. 1088-1094.
Yoon et al., "Syntheses and cytotoxicities of four stereoisomers of muricatacin from Dglucose," Bioorganic and Medicinal Chemistry, 1998, 6(7), pp. 1043-1049.
Streicher et al., "Synthesis of functionalized cyclohexenephosphonates and their inhibitory activity towards bacterial sialidases," Tetrahedron, Elsevier Science Publishers, Amsterdam, NL, Sep. 16, 2002, vol. 58 No. 38, pp. 7573-7581.
Search Report, Chinese Application No. 200980154858.0, mailed Feb. 4, 2013.
International Search Report and Written Opinion, International Application No. PCT/US09/64605, dated Jan. 22, 2010.
Zhu, et al., "Preparation of Monoacetylated Diols via Cyclic Ketene Acetals," Journal of Organic Chemistry, pp. 5729-5731, 1995.
Kloth et al., Adv. Synth. Catal. 2005, 347, 1423-34.
House, H.O., Modern Synthetic Reactions, 1965, pp. 2-5.
Steglich et al., Angew. Chem. Internat. Edit., 1969, 8(12), 981.
Australian Examination Report; Jul. 23, 2014.
Chemlookup.com; CAS-RN-80244-96-8.

* cited by examiner

*Primary Examiner* — Ganapathy Krishnan
(74) *Attorney, Agent, or Firm* — Mintz, Levin, Cohn, Ferris, Glovsky And Popeo, P.C.

(57) ABSTRACT

The invention relates to methods for making deoxyribofuranose compounds such as compound (2) which are useful intermediates in the preparation of pharmaceutical compounds such as 5-amino-3-(2'-O-acetyl-3'-deoxy-β-D-ribofuranosyl)-3H-thiazolo[4,5-d]pyrimidin-2-one and the like.

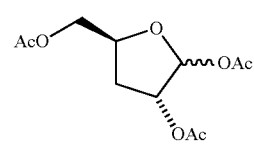

2

1 Claim, No Drawings

METHOD OF PREPARING DEOXYRIBOFURANOSE COMPOUNDS

CROSS-REFERENCE TO RELATED APPLICATIONS

The present application is a divisional application of U.S. application Ser. No. 13/129,730 filed Aug. 9, 2011, which is a national stage application of International Application Number PCT/US09/64605 filed Nov. 16, 2009, which claims the benefit of U.S. Provisional Application No. 61/115,134, filed Nov. 17, 2008, the entire contents of which are incorporated herein.

FIELD OF THE INVENTION

The invention relates to methods for making deoxyribofuranose compounds which are useful intermediates in the preparation of pharmaceutical compounds such as 5-amino-3-(2'-O-acetyl-3'-deoxy-β-D-ribofuranosyl)-3H-thiazolo[4,5-d]pyrimidin-2-one and the like.

BACKGROUND OF THE INVENTION

Nucleoside analogs are an important class of compounds that are useful in the treatment of disease. For example, nucleoside analogs have been used in the treatment of cancers and viral infections. After entry into a cell, nucleoside analogs are frequently phosphorylated by nucleoside salvage pathways in which the analogs are phosphorylated to the corresponding mono-, di-, and triphosphates. Among other intracellular destinations, triphosphorylated nucleoside analogs often serve as substrates for DNA or RNA polymerases and become incorporated into DNA and/or RNA. Where triphosphorylated nucleoside analogs are strong polymerase inhibitors, they may induce premature termination of a nascent nucleic acid molecule. Where triphosphorylated nucleoside analogs are incorporated into nucleic acid replicates or transcripts, gene expression or disruption of function may result.

Some nucleoside analogs may be efficacious because of their ability to inhibit adenosine kinase. Adenosine kinase catalyzes the phosphorylation of adenosine to adenosine 5'-monophosphate (AMP). Inhibition of adenosine kinase may effectively increase the extracellular level of adenosine in humans and thereby serve as a treatment of ischemic conditions such as stroke, inflammation, arthritis, seizures, and epilepsy.

The last few decades have seen significant efforts expended in exploring therapeutic uses of nucleoside analogs. For example, certain pyrimido[4,5-d]pyrimidine nucleosides are disclosed in U.S. Pat. No. 5,041,542 to Robins et al. as being effective in treatment against L1210 in BDF1 mice. Additionally, 3-β-D-ribofuranosylthiazolo[4,5-d]pyrimidines demonstrating significant immunoactivity, including murine spleen cell proliferation and in vivo activity against Semliki Forest virus, are disclosed in U.S. Pat. Nos. 5,041,426 and 4,880,784 to Robins et al. A number of publications have also described non-glycosyl derivatives of the thiazolo[4,5-d]pyrimidine moiety. See, e.g., U.S. Pat. Nos. 5,994,321 and 5,446,045; Revankar et al., J. HET. CHEM., 30, 1341-49 (1993); and Lewis et al., J. HET. CHEM., 32, 547-56 (1995).

3,5-Disubstituted-3H-thiazolo[4,5-d]pyrimidin-2-one compounds have been shown to have immunomodulatory activity. The preparation and usefulness of this class of compounds is discussed in U.S. Application Publication No. US2006/0160830 (U.S. application Ser. No. 11/304,691), and U.S. application Ser. No. 11/873,202, both of which are incorporated herein by reference in their entireties.

SUMMARY OF THE INVENTION

The invention is directed to a method for preparing compound (2)

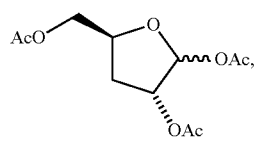

comprising
(i) reacting compound (4) with an alkyl ketene acetal and catalytic acid

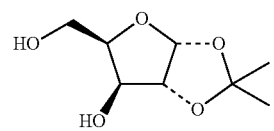

to form a cyclic compound of Formula (5)

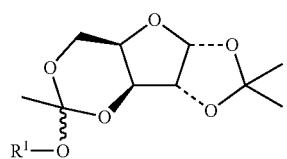

wherein $R^1$ is a lower alkyl,
(ii) hydrolysing the compound of Formula (5) with water and a catalytic or stoichiometric amount of acid to form a mixture of monoacyl substituted compounds (6) and (7),

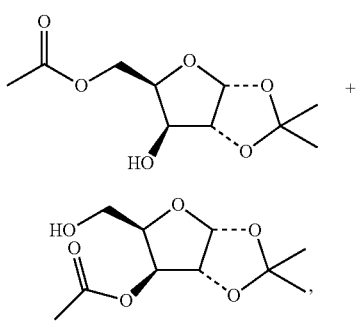

(iii) equilibrating the mixture of monoacyl substituted compounds (6) and (7) to cause an excess of compound (6),
(iv) oxidizing the mixture of compound 6 and compound 7 to form the mixture of ketone of compound (8) and hydrated ketone of compound (9)

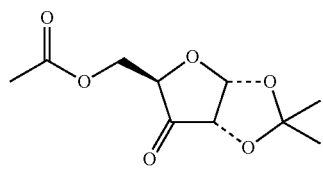

8

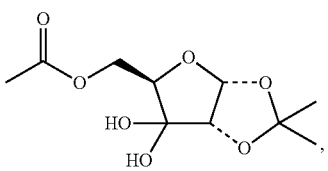

9

(v) reducing the mixture of ketone of compound (8) and hydrated ketone of compound (9) to form compound (10) or reducing compound (8) and compound (9) separately to form compound (10)

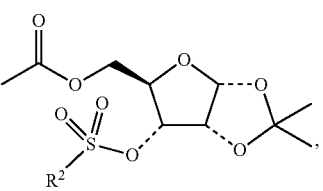

10

(vi) sulfonating compound (10) with a sulfonating agent in the presence of a base to form compound of Formula (11)

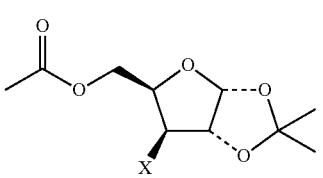

11 wherein $R^2$ is an optionally substituted alkyl or aryl, (vii) displacing the sulfonate ester compound of Formula (11) with a halogen atom to form a halogen compound of Formula (12)

12 wherein X is halo, (viii) reducing the halogen of the Formula (12) compound to a hydrogen atom to form compound (13)

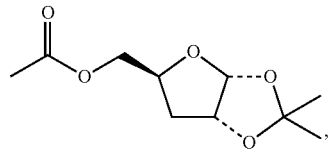

13 and (ix) treating compound (13) with an acid catalyst and acylating agent to form compound (2).

In one embodiment of the invention, $R^1$ is —$CH_3$ or —$CH_2CH_3$.

In one embodiment of the invention, $R^2$ is an optionally substituted $C_1$-$C_6$ alkyl or phenyl. In another embodiment, $R^2$ is —$CF_3$, —$CH_3$, or —$C_6H_4CH_3$. In another embodiment $R^2$ is —$CF_3$.

In another embodiment, the invention relates to a method of reacting compound (4) with ketene dimethylacetal in the presence of catalytic methanesulfonic acid to form tricycle compound (5A) in isopropyl acetate

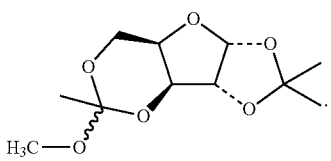

5A

In another embodiment the invention is drawn to a method of preparing a mixture of mono acetylated compounds (6) and (7) by treating compound (5A) with water and 1 mole percent of methane sulfonic acid.

In another embodiment the invention is drawn to a method of equilibrating a mixture of compounds (6) and (7) to cause an excess of compound (6) by heating above 70° C.

In another embodiment the invention is drawn to a method of equilibrating a mixture of compounds (6) and (7) to cause an excess greater than 90% of compound (6) over compound (7).

In another embodiment the invention is drawn to a method of equilibrating a mixture of compounds (6) and (7) to favor compound (6) by heating above 70° C. in the presence of isopropyl acetate and water.

In another embodiment the invention is drawn to a method of oxidizing a mixture of compounds (6) and (7) to form compound (8) and its hydrated form (9).

In another embodiment the invention is drawn to a method of oxidizing a mixture of compounds (6) and (7) to form compound (8) and its hydrated form (9) by using sodium hypochlorite in the presence of TEMPO and sodium acetate biphasically with isopropyl acetate.

In another embodiment the invention is drawn to a method of reducing compounds (8) or (9) or a mixture thereof to form compound (10) as a single isomer.

In another embodiment the invention is drawn to a method of reducing a mixture of compounds (8) and (9) to form compound (10) as a single isomer using sodium triacetoxyborohydride.

In another embodiment the invention is drawn to a method of reducing a mixture of compounds (8) and (9) to form compound (10) as a single isomer using sodium triacetoxyborohydride in wet isopropyl acetate.

In another embodiment the invention is drawn to a method of isolating compound (8) from compound (9).

In another embodiment the invention is drawn to a method of reducing compound (8) to form compound (10) as a single isomer.

In another embodiment the invention is drawn to a method of reducing compound (8) to form compound (10) as a single isomer using a platinum on carbon catalyst in the presence of hydrogen.

In another embodiment the invention is drawn to a method of sulfonating compound (10) with a sulfonating agent in the presence of DMAP to form a compound of Formula (11).

In another embodiment the invention is drawn to a method of sulfonating compound (10) with a trifluoromethanesulfonic anhydride in the presence of DMAP to form compound (11A) without the use of halogenated solvents or temperatures below 0° C.

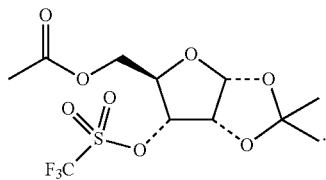

11A

In another embodiment the invention is drawn to a method of sulfonating compound (10) with trifluoromethanesulfonic anhydride in the presence of DMAP to form compound (11A) in a mixture of isopropylacetate and dimethoxyethane at 5-10° C.

In another embodiment the invention relates to a method of displacing sulfonyl substituted compound (11A) with iodide at less than 60° C. in lower boiling organic solvents to form compound (12A)

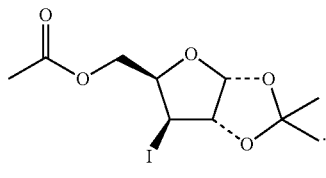

12A

In another embodiment the invention relates to a method of displacing sulfonyl substituted compound (11A) with sodium iodide in wet isopropyl acetate and dimethoxyethane at 55° C. to form compound (12A).

In another embodiment the invention is drawn to a method of reducing compound (12A) to form hydrogen compound (13).

In another embodiment the invention is drawn to a method of reducing compound (12A) to form hydrogen compound (13) using catalytic hydrogenation.

In another embodiment the invention is drawn to a method of reducing compound (12A) to form hydrogen compound (13) using palladium hydroxide on carbon (Pearlman's Catalyst) in the presence of hydrogen.

In another embodiment the invention is drawn to a method of reducing compound (12A) to form hydrogen compound (13) using hydrogen and catalytic palladium hydroxide on carbon (Pearlman's Catalyst) in the presence of an amine base such as diisopropylethylamine or triethylamine.

In another embodiment the invention is drawn to a method of reducing compound (12A) to form hydrogen compound (13) using hydrogen and catalytic palladium hydroxide on carbon (Pearlman's Catalyst) in the presence of diisopropylethylamine in ethanol and isopropyl acetate.

In another embodiment the invention is drawn to a method of reducing compound (12A) to form hydrogen compound (13) using hydrogen and catalytic palladium on carbon in the presence of triethylamine in ethyl acetate.

In another embodiment the invention is drawn to a method of treating compound (13) with a catalytic amount of sulfuric acid and adding over 12 hours acetic anhydride as an acylating agent in acetic acid to form compound (2).

The method of the invention is particularly useful for the scalable commercial production of the compounds described herein. The methods are operationally simple, robust and efficient. In particular, the methods are particularly useful for scaled-up production of deoxy sugars. Furthermore, the methods are cost-effective and demonstrate efficient throughput and a significantly higher overall yield as compared to the preparation methods used in the art.

DETAILED DESCRIPTION OF THE INVENTION

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

As used herein, the term "halide" or "halo" refers to fluoride, chloride, bromide and iodide. The term halogen refers to fluorine, chlorine, bromine and iodine.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "aryl", as used herein, unless otherwise indicated, includes an organic radical derived from an aromatic hydrocarbon by removal of one hydrogen, such as phenyl or naphthyl.

The "alkyl" and "aryl" groups are optionally substituted by 1-5 substituents selected from —OH, halo, —CN, $C_1$-$C_6$ alkyl, arylalkyl, $C_1$-$C_6$ alkoxy, $C_1$-$C_6$ alkenyl, $C_1$-$C_6$ hydroxyl, $C_1$-$C_6$ hydroxyalkyl, amino, $C_1$-$C_6$ alkylamine, $C_1$-$C_6$ dialkylamine, wherein the alkyl groups can be further substituted with one or more halogens.

The term "Ac" means acetyl.

The term "alkyl ketene acetal" means 1,1-dialkoxyethene.

The term "catalytic" means of involving or acting as a catalyst.

The term "stoichiometric" means an equivalent amount.

The compounds of the disclosure may exist as single stereoisomers, racemates and/or variable mixtures of enantiomers and/or diastereomers. All such single stereoisomers, racemates and/or variable mixtures of enantiomers and/or diastereomers are intended to be within the scope of the present disclosure.

As used herein, the term "oxidizing agent" refers to a substance or species that gains electrons in a chemical reaction and the term "reducing agent" refers to a substance that loses electrons in a chemical reaction.

The term "immunomodulator" refers to natural or synthetic products capable of modifying the normal or aberrant immune system through stimulation or suppression.

The terms "R" and "S" indicate the specific stereochemical configuration of a substituent at an asymmetric carbon atom in a chemical structure as drawn.

The compounds of the invention may exhibit the phenomenon of tautomerism. While the formulae set forth herein cannot expressly depict all possible tautomeric forms, it is to be understood that the formulae set forth herein are intended to represent any tautomeric form of the depicted compound and is not to be limited merely to a specific compound form depicted by the formula drawings.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Compound (2) is useful as an intermediate in the preparation of a pharmaceuticals compounds such as 5-amino-3-(2'-O-acetyl-3'-deoxy-β-D-ribofuranosyl)-3H-thiazolo[4,5-d]pyrimidin-2-one (3) and pharmaceutically acceptable salts thereof. As described in U.S. application Ser. No. 11/873,202, the deoxyribofuranose compound (2) is coupled with 5-amino-3H-thiazolo[4,5-d]pyrimidin-2-one (1) to form compound (3)

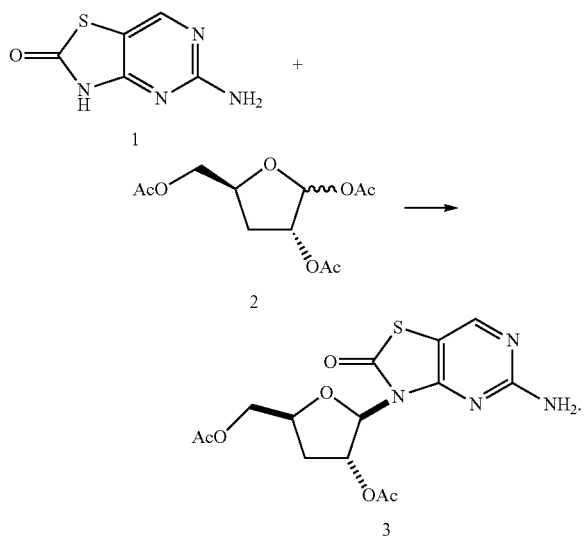

Compound (3) is used in methods for treating or preventing disease. For instance, compound (3) is used in methods of treating or preventing the onset and/or progression of tumors or cancers. Also disclosed are methods of treating or preventing infection by a pathogen such as, for example, viruses including Hepatitis B virus or Hepatitis C virus. Compound (3) is also used in methods of modulating immune cytokine activity.

EXAMPLES

The following examples are for illustrative purposes only and are not intended to limit the scope of the claims.

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of nitrogen or argon at an ambient temperature (unless otherwise stated) in anhydrous solvents, and the reaction flasks were fitted with rubber septa for the introduction of substrates and reagents via syringe or an addition funnel for liquids or a powder funnel for solids.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, para-anisaldehyde solution with acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures may utilize many common chemical abbreviations, DME (1,2-dimethoxy ethane), MTBE (methyl tert-butyl ether), TEMPO (2,2,6,6-Tetramethylpiperidine 1-oxyl), 2,2-DMP (2,2-dimethoxypropane), Ac (acetyl), ACN (acetonitrile), Bn (benzyl), BOC (tert-butoxycarbonyl), Bz (benzoyl), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N', N'-tetramethyluronium hexafluorophosphate), HF (hydrogen fluoride), HOBT (1-hydroxybenzotriazole hydrate), HPLC (high pressure liquid chromatography), IPA (isopropyl alcohol), KO'Bu (potassium tert-butoxide), LDA (lithium diisopropylamide), MCPBA (3-chloroperoxybenzoic acid), Me (methyl), MeCN (acetonitrile), MeOH (methanol), NaH (sodium hydride), NaOAc (sodium acetate), NaOEt (sodium ethoxide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Example 1

Preparation of Compound (6) (Major) and Compound (7) (Minor)

(a) Step 1: Formation of Tricycle Compound (5A)

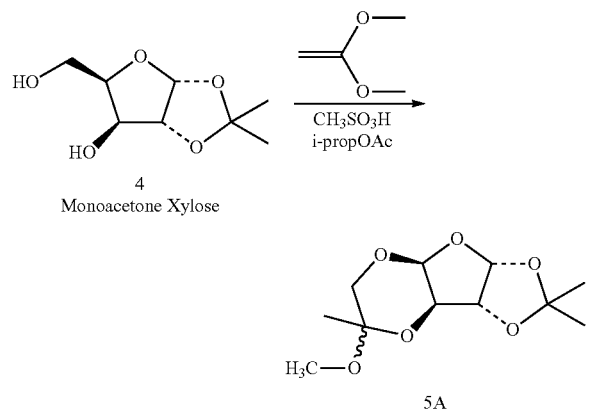

4
Monoacetone Xylose

5A

A 4 liter 4 necked flask equipped with a nitrogen inlet, addition funnel, thermometer, and mechanical stirrer was charged with monoacetonexylose (152.16 grams, 800 mmol) and isopropylacetate (1200 ml) and stirred until the solids dissolved, yielding a slightly cloudy solution. Ketenedimethylacetal (3.36 ml, 35.5 mmol) was added and the reaction cooled to 3° C. using an ice bath. Methanesulfonic acid (0.52 ml, 8 mmol) was added followed by the dropwise addition of ketenedimethylacetal (80 ml, 844.5 mmol) over 45 minutes. The reaction temperature reached 10° C. during the addition. When the addition was complete TLC, using 80% MTBE in hexane, indicated a complete, clean conversion to the much faster running tricycle 5A. The ice bath was removed.

(b) Step 2: Hydrolysis of Compound 5A to a Mixture of Monoacetates

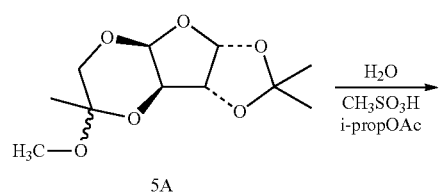

5A

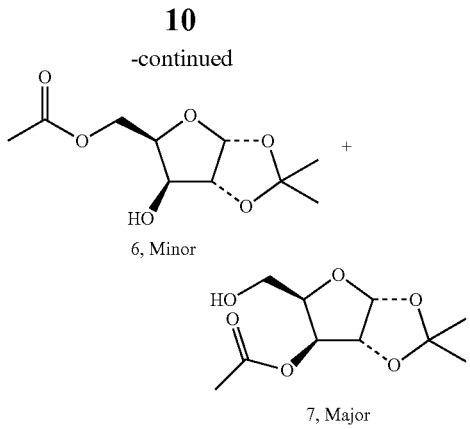

6, Minor

7, Major

Water (72 ml, 4000 mmol) was added all at once to the above reaction and the mixture stirred at ambient temperature for 90 minutes. The TLC of the reaction using 80% MTBE in hexane indicated two new mid-polarity products were formed with the slower running of the two being the major product.

The reaction was transferred to a 2 liter separatory funnel and shaken with a 120 ml of an aqueous solution (60 ml 1.0M NaHCO$_3$, 60 ml 30% NaCl), the phases split and the organic phase was transferred to a round bottom flask and the volatiles were removed in vacuo.

(c) Step 3: Equilibration to Compound (6).

The material isolated from the evaporation was reconstituted in fresh isopropylacetate (1200 ml) and water (72 ml) and heated to 77° C. for 12 hours, then cooled to ambient temperature. A TLC analysis using 80% MTBE in hexane indicated that the faster running of the two products is the major product with only a trace of the slower running isomer present.

A 0.2 ml sample of the reaction mixture was evaporated to dryness to yield 37 mg of a solid. $^1$H NMR confirms that the desired acetate compound (6) is the very major product. $^1$H NMR (400 MHz, CDCl$_3$) δ: 5.92 (1H, d, J=3.3 Hz), 4.51-4.56 (2H, m), 4.24-4.28 (1H, m), 4.13-4.19 (2H, m), 2.98 (1H, d, J=4.0 Hz), 2.11 (3H, s), 1.51 (3H, s), 1.33 (3H, s).

Example 2

Preparation of Compounds (8) and (9)

The 4 liter flask that already contains approximately 0.8 Moles of compound (6) in wet isopropylacetate from the previous step was equipped with a nitrogen inlet, thermometer, addition funnel and a mechanical stirrer. TEMPO (800 mg) was added and the mixture was stirred and cooled in an ice bath. In a separate flask an aqueous solution containing 64.3 grams of sodium bromide, 98.4 grams of sodium acetate dissolved in 320 ml of deionized water was cooled to 5° C. When the reaction temperature reached 5° C. the pre-cooled aqueous solution was added to it to form a biphasic reaction mixture. To this cold solution was added dropwise 735 ml of aqueous sodium hypochlorite solution (titrated directly before use, 10.15% or 1.36M, 1.002 Moles, 1.25 equivalents) over 2 hours, keeping the exothermic addition at or below 7° C. When the addition was complete stirring was continued for 30 minutes and the TLC (80% MTBE-hexane) indicated a complete conversion to the slower running ketone.

The reaction was transferred to a 4 liter separatory funnel and the phases split. The dark organic portion was washed once with 160 ml of aqueous 2.5% sodium thiosulfate solution. The resulting pale yellow organic portion was washed with 160 ml of 30% sodium chloride solution. The aqueous phases were combined and 44.1 grams of solid sodium chloride was added and stirred until all of the salt dissolved. The resulting aqueous solution was extracted twice with 400 ml portions of isopropylacetate, the organic extracts were combined, and washed once with 50 ml of 30% sodium chloride solution. All of the organic portions were combined to give a slightly cloudy solution.

A 0.25 ml portion of this solution was evaporated to give 14 mg of a solid. $^1$H NMR confirms the presence of both the ketone and the hydrate as an approximately 1:1 mixture. $^1$H NMR (400 MHz, CDCl$_3$) δ: 6.09 (1H, d, J=4.4 Hz, Compound 8), 5.84 (1H, d, J=3.9 Hz, Compound 9), 4.61 (1H, dd, J$_1$=11.7 Hz, J$_2$=6.3 Hz, Compound 9), 4.56 (1H, t, J=3.3 Hz, Compound 8), 4.36-4.42 (2H, m, Compounds 8 and 9), 4.20-4.24 (2H, m, Compounds 8 and 9), 4.06-4.15 (2H, m, Compounds 8 and 9), 2.11 (3H, s, Compound 9), 2.05 (3H, s, Compound 8), 1.58 (3H, s, Compound 9), 1.50 (3H, s, Compound 8), 1.43 (3H, s, Compound 8), 1.36 (3H, s, Compound 9).

Example 3

Preparation of Compound (10)

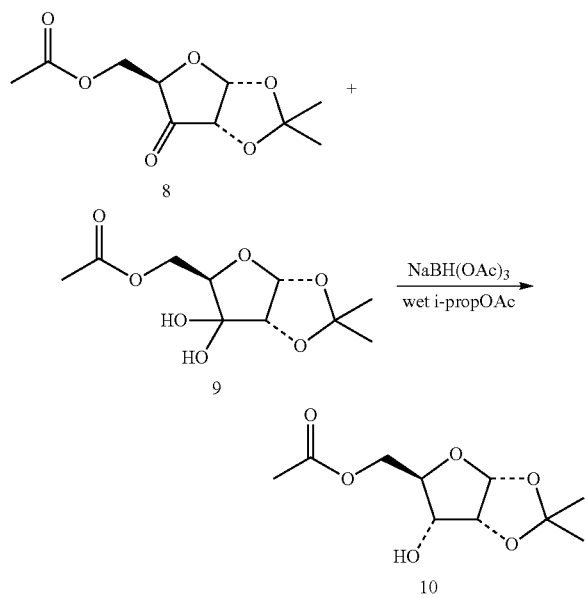

A 4 liter 4-necked flask equipped with a nitrogen inlet, powder funnel, thermometer, and mechanical stirrer was charged with the cloudy organic solution of ketone (8) and its hydrate (9). This was cooled while stirring to 4° C. using an ice bath. To this cold solution was added four 42.4 gram portions of solid sodium triacetoxyborohydride in 15 minute intervals. After the final addition the reaction was stirred at 5° C. for 60 minutes.

While stirring at 5° C. 1.0 M aqueous sodium carbonate solution (800 ml) was added quickly. The reaction temperature rises to 12° C. and a small amount of gas evolution occurs. The mixture thickens substantially. After stirring 15 minutes the reaction is transferred to a 4 liter separatory funnel and the phases split, the aqueous portion contains some solid. The organic portion was stirred with 2.0 M aqueous sodium carbonate solution (400 ml) for 10 minutes, the phases split and both aqueous phases were combined. The solid in the aqueous phase was filtered and then was dissolved in water (600 ml) and added back to the resulting homogeneous aqueous phase. The aqueous phase was extracted with two 200 ml portions of isopropylacetate and the organic portions were combined. The total weight of the organic phase was 2,370.5 grams.

A 5 gram portion of the organic phase was evaporated to give 243 mg of oil that crystallized under vacuum. Calculated yield: 2370.5 grams solution×0.243 grams product/5 grams solution=115.2 grams (496.15 mmol, 62%) of compound 10. $^1$H NMR indicates this is a very pure sample. $^1$H NMR (400 MHz, CDCl$_3$) δ: 5.82 (1H, d, J=3.9 Hz), 4.58 (1H, t, J=4.3 Hz), 4.43 (1H, dd, J$_1$=12.4 Hz, J$_2$=2.4 Hz), 4.16-4.20 (1H, m), 3.93-3.97 (1H, m), 3.81-3.87 (1H, m), 2.45 (1H, d, J=10.8 Hz), 2.10 (3H, s), 1.58 (3H, s), 1.38 (3H, s).

A 4 liter 4-necked flask equipped with a short path distillation head, a temperature probe and mechanical stirring was charged with the 2,370.5 gram organic phase. This was heated to remove 2400 ml of distillate at atmospheric pressure. Fresh isopropylacetate (1500 ml) was added to the flask and 1500 ml were removed by distillation. The reaction flask was then diluted with 920 ml of isopropylacetate to give a slightly cloudy solution. This solution is now ready to be taken to the next step.

Example 4

Alternative Preparation of Compounds (8) and (10)

(a) Step 1: Preparation of Compound (8)

The flask that contained Compound 6 (approximately 0.2 mol in wet isopropyl acetate from Example 1 was equipped with a nitrogen inlet, thermometer, addition funnel and a magnetic stirrer. TEMPO (200 mg) was added and the mixture was stirred and cooled in a 0° C. ice bath. In a separate flask an aqueous solution containing sodium bromide (16.08 g) and sodium acetate (24.6 g) dissolved deionized water (80 mL) was cooled to 5° C. When the reaction temperature reached 5° C. the pre-cooled aqueous solution was added to it to form a biphasic reaction mixture.

To this cold mixture was added dropwise an aqueous sodium hypochlorite solution (labeled 10-15%; 180 mL) over 1 h, keeping the exothermic addition at or below 7° C. When the addition was complete TLC (80% MTBE-hexanes) indicated a complete conversion to the lower R$_f$ ketone. The cooling bath was removed and solid NaCl (25 g) was added. After stirring for 30 min., the mixture was transferred to a 1-L separatory funnel and the phases were then separated. The dark organic portion was shaken with 1.0 M NaHCO$_3$ (25 mL), and then 2.0 M Na$_2$SO$_3$ (30 mL) was added and shaking was continued until all of the color dissipated (some outgassing occurred).

The resulting clear organic portion was washed once with 15% aqueous NaCl (20 mL). The clear organic phase was transferred to a 1-L flask equipped with a temperature probe, a distillation head, and magnetic stirring. The temperature was set to 85° C. to distill the solvent. When the distillation stopped, the temperature was raised to 105° C. to complete the distillation. The distillation flask was cooled to ambient temperature and the mixture was diluted with isopropylacetate (100 mL). Activated carbon (Darco G60; 5 g) was added and the mixture was stirred at ambient temperature for 90 min. This mixture was filtered using Celite and the solids were washed with isopropyl acetate (2×30 mL). The pale yellow filtrate weighed 220.5 g. 2.0 mL of this solution (weight=1.826 g) was evaporated to yield 0.189 g of a pale yellow oil. Calculation showed a solution concentration of 0.41 M of Compound 8 and total yield of 22.86 g (49.6% from monoacetone xylose). $^1$H NMR (400 MHz, CDCl$_3$) δ: 1.43 (3H, s), 1.50 (3H, s), 2.05 (3H, s), 4.21 (1H, dd, $J_1$=11.9 Hz, $J_2$=3.9 Hz), 4.37 (1H, d, J=4.7 Hz), 4.40 (1H, dd, $J_1$=12.5 Hz, $J_2$=3.2 Hz), 4.56 (1H, t, J=3.1 Hz), 6.09 (1H, d, J=3.8 Hz). $^1$H-NMR showed that only Compound 8 was present (Compound 9 was absent).

b. Step 2: Preparation of Compound (10)

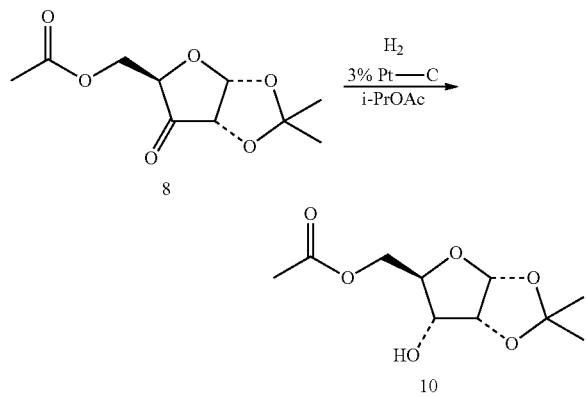

A 250-mL three-necked round bottom flask equipped with a temperature probe, a balloon filled with hydrogen gas, and magnetic stirring, was charged 62 mL of the 0.41 M solution of compound 8 prepared above and wet 3% Pt-C (2.05 g, Johnson Matthey type B101018-3, lot C-9264, 58.25% water). The temperature was equilibrated to 26° C., the mixture degassed with house vacuum and flushed with hydrogen gas three times, and the mixture was then stirred vigorously under a hydrogen atmosphere for 16 h. GC analysis indicated a complete conversion to Compound 10. The solution was filtered through Celite filter aid, the solids were washed with isopropyl acetate (2×30 mL), and the clear, colorless filtrate was then evaporated to give 5.74 g of oil that crystallized. $^1$H-NMR confirmed Compound (10) as the only product.

Example 5

Preparation of Compound (11A)

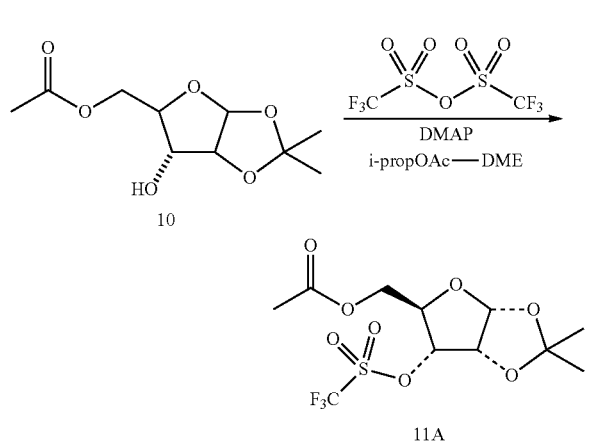

The 4 liter flask that already contains approximately 496.15 mmol of compound 10 in dry isopropylacetate from Example 3 was equipped with a nitrogen inlet, thermometer, rubber septum and a mechanical stirrer. In a separate flask DMAP (90.92 grams, 744.23 mmol, 1.5 eq) was dissolved in 255 ml of hot DME. The hot solution was added to the reaction flask and the reaction was cooled in an ice bath to 5° C. Trifluoromethanesulfonic anhydride (104.34 ml, 620.19 mmol, 1.25 eq) was added at 1.17 ml/minute using a syringe pump. The maximum temperature reached during the addition was 7° C. When the addition was complete and the reaction temperature returned to 5° C. a TLC (20% EtOAc-Toluene) indicated a complete, clean conversion to the faster running triflate.

To the 5° C. reaction was added 1.0M HCl (745 ml) causing a 9° C. exotherm. After stirring 5 minutes the reaction was transferred to separatory funnel and the phases split. The organic phase was washed with two portions of 1.0 M HCl (300 ml) and once with 240 ml of an aqueous solution (120 ml 1.0 M NaHCO$_3$, 120 ml 30% sodium chloride). All of the aqueous phases were combined and extracted once with 500 ml of isopropylacetate. The extract was washed with two 100 ml portions of 1.0 M HCl and once with 80 ml of aqueous solution (40 ml 1.0 M NaHCO$_3$, 40 ml 30% sodium chloride). All of the organic phases were combined to get a slightly cloudy solution of the triflate 11A.

A 0.25 ml portion of this solution was evaporated to get 22 mg of an oil. $^1$H NMR indicates this is a very pure sample of the triflate along with a small amount of residual isopropylacetate. $^1$H NMR (400 MHz, CDCl$_3$) δ: 5.85 (1H, d, J=3.9 Hz), 4.85 (1H, dd, $J_1$=8.6 Hz, $J_2$=4.6 Hz), 4.77 (1H, t, J=4.3 Hz), 4.37-4.42 (2H, m), 4.22-4.26 (1H, m), 2.11 (3H, s), 1.61 (3H, s), 1.40 (3H, s).

Example 6

Preparation of Compound (12A)

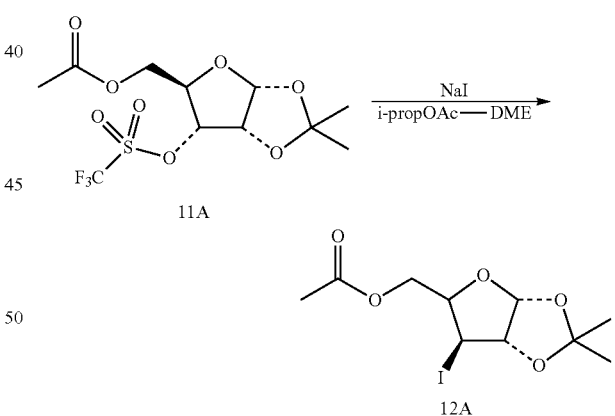

A 4 liter 4 necked flask equipped with a nitrogen inlet, temperature probe, condenser and mechanical stirrer was charged with the isopropylacetate solution of the triflate (assumed to be 496.15 mmol) and 255 ml of DME. Solid sodium iodide (111.55 grams, 744.23 mmol, 1.5 eq) was added and the mixture stirred at 55° C. for 17 hours. A TLC (10% EtOAc-Toluene) indicates a complete conversion to iodide.

Water (400 ml) was added and the mixture stirred rapidly for five minutes. The mixture was transferred to a separatory funnel and the phases split. The organic phase was washed once with 400 ml of an aqueous solution (200 ml of 1.0M NaHCO$_3$ and 200 ml of 30% NaCl). The aqueous phases were combined and extracted once with the isopropylacetate (400 ml). The extract was washed once with water (100 ml) and once with 100 ml of aqueous solution (50 ml of 1.0M NaHCO$_3$ and 50 ml of 30% NaCl). All of the organic phases were combined.

The solution of compound 12A was transferred to a 3 liter round bottom flask equipped with a short path distillation head. Two liters of solvent were removed by simple distillation. The mixture was cooled to ambient temperature and the residual volume was determined to be 500 ml. To this was added 183 ml of isopropylacetate and 208 ml of 200 proof ethanol to generate a 0.5M solution of compound 12A in a 20% ethanol/isopropylacetate solution.

A 0.2 ml aliquot was removed and evaporated to get 42 mg of an oil. $^1$H NMR indicates this is a very pure sample of compound 12A. $^1$H NMR (400 MHz, CDCl$_3$) δ: 6.02 (1H, d, J=2.9 Hz), 5.04 (1H, d, J=2.9 Hz), 4.35 (1H, d, J=3.1 Hz), 4.15-4.24 (2H, m), 3.77-3.80 (1H, m), 2.10 (3H, s), 1.52 (3H, s), 1.33 (3H, s).

Example 7

Preparation of Compound (13)

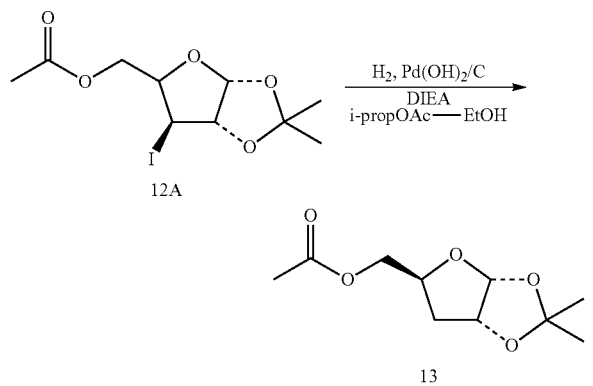

A 3 liter round bottom flask equipped with a large magnetic stir bar was charged with the solution of compound 12A (assumed 496.15 mmol as a 0.5 M solution in 20% ethanol/isopropylacetate), Diisopropylethylamine (112.34 ml, 644.8 mmol, 1.3 eq) and 20.37 grams of 20% Pd(OH)$_2$/C (Pearlman's Catalyst). While stirring rapidly the reaction was degassed with a light vacuum and then filled with hydrogen gas three times. The reaction was then stirred under an atmosphere of hydrogen for 18 hours. A TLC (10% EtOAc-toluene) indicated a clean, complete conversion to the slower running hydrogen compound.

The reaction was filtered through Celite and the dark solids washed with two 200 ml portions of isopropylacetate. The filtrate was transferred to a 4 liter separatory funnel and washed once with 1.0 M HCl (645 ml), once with 200 ml of an aqueous solution (100 ml 2.5% sodium thiosulfate, 100 ml 1.0M NaHCO$_3$) and once with 200 ml of 30% NaCl. All of the aqueous phases were combined and extracted with two 200 ml portions of isopropylacetate. The extracts were combined and washed once with 80 ml of an aqueous solution (40 ml 2.5% sodium thiosulfate, 40 ml 1.0M NaHCO$_3$) and once with 80 ml of 30% NaCl. The organic portions were combined, transferred to a 3 liter round bottom flask and 1.5 liters of solvent was removed by atmospheric distillation. The cooled residue had a volume of 450 ml. 50 ml of isopropylacetate was added to form a solution close to 1.0 M and 10 grams of Norit charcoal was added and the mixture stirred two hours at ambient temperature.

This was then filtered through Celite to give a clear, golden colored filtrate. The filtrate was concentrated in vacuo to give 103.47 grams (478.52 mmol) of a golden colored clear oil. $^1$H NMR indicates a very high purity of compound 13. $^1$H NMR (400 MHz, CDCl$_3$) δ: 5.83 (1H, d, J=3.7 Hz), 4.74 (1H, t, J=4.2 Hz), 4.39-4.45 (1H, m), 4.28 (1H, dd, J$_1$=11.8 Hz, J$_2$=3.1 Hz), 4.08 (1H, dd, J$_1$=12.5 Hz, J$_2$=6.2 Hz), 2.07-2.12 (4H, m), 1.62-1.69 (1H, m), 1.52 (3H, s), 1.33 (3H, s).

Compound 13 can be further purified by vacuum distillation if required. BP=70° C. at 0.025 mm Hg.

Example 8

Preparation of Compound (2)

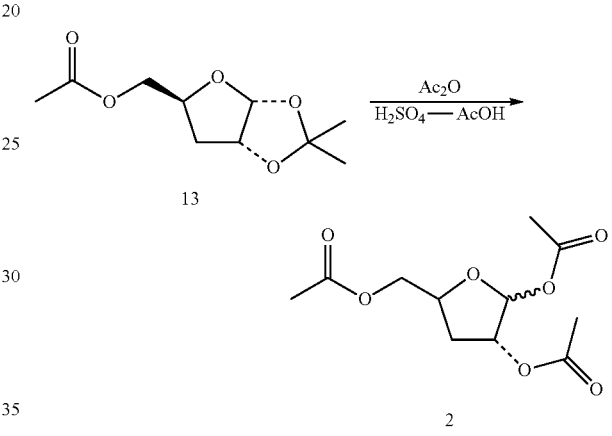

A 25 ml round bottom flask equipped with magnetic stirring and a rubber septum was charged with compound 13 (640 mg, 2.96 mmol) and 5 ml of acetic acid. In a separate flask acetic anhydride (0.562 ml, 6 mmol, 2 eq) was diluted to a total volume of 2.0 ml with acetic acid and 0.1 ml of this acetic anhydride solution was added to the reaction mixture. Sulfuric acid (0.15 ml of a 1.0M solution in acetic acid, 0.15 mmol, 0.05 eq) was added to the reaction, and then the balance of the acetic anhydride solution (1.9 ml) was added over 12 hours using a syringe pump. A TLC (30% EtOAc-hexane) shows a very clean conversion to the desired compound 2.

It is important to note that the construction and arrangement of the methods and steps shown in the exemplary embodiments is illustrative only. Although only a few embodiments of the present disclosure have been described in detail, those skilled in the art will readily appreciate that many modifications are possible without materially departing from the novel teachings and advantages of the subject matter recited in the claims. Accordingly, all such modifications are intended to be included within the scope of the present disclosure as defined in the appended claims. The order or sequence of any method or method steps may be varied or re-sequenced according to alternative embodiments. Other substitution, modification, changes and omissions may be made in the design, operating conditions and arrangement of the embodiments without departing from the spirit of the present disclosure as expressed in the appended claims.
I claim:
1. The compound
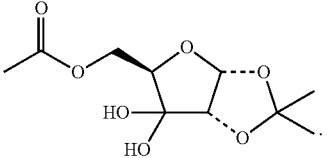

The reaction was diluted with toluene and evaporated in vacuo. The residue was dissolved in MTBE, stirred with 10% sodium carbonate for 15 minutes and the phases split. The organic portion was dried (MgSO$_4$), filtered through a small pad of silica gel and evaporated to get 680 mg (2.61 mmol) of a clear oil. $^1$H NMR shows this to be a clean mixture of both anomers.